(12) United States Patent
Osgood et al.

(10) Patent No.: US 6,355,934 B1
(45) Date of Patent: *Mar. 12, 2002

(54) IMAGING SYSTEM FOR AN OPTICAL SCANNER

(75) Inventors: Avery Osgood, Bellingham; Mack Schermer, Belmont, both of MA (US)

(73) Assignee: Packard BioChip Technologies, Billerica, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/258,484

(22) Filed: Feb. 26, 1999

(51) Int. Cl.$^7$ .............................................. G01N 21/64
(52) U.S. Cl. .................................... 250/458.1; 250/216
(58) Field of Search ............................. 250/458.1, 216

(56) References Cited

U.S. PATENT DOCUMENTS

| | | | |
|---|---|---|---|
| 4,122,348 A | 10/1978 | Bruck | 250/461 |
| 4,407,008 A * | 9/1983 | Schmidt et al. | 358/93 |
| 5,022,757 A | 6/1991 | Modell | 356/318 |
| 5,329,461 A | 7/1994 | Allen et al. | 364/497 |
| 5,381,224 A | 1/1995 | Dixon et al. | 356/72 |
| 5,399,866 A | 3/1995 | Feldman et al. | 250/458 |
| 5,437,840 A | 8/1995 | King et al. | |
| 5,556,764 A | 9/1996 | Sizto et al. | |
| 5,631,734 A | 5/1997 | Stern et al. | 356/317 |
| 5,672,880 A | 9/1997 | Kain | 250/458.1 |
| 5,719,391 A | 2/1998 | Kain | 250/235 |
| 6,121,603 A * | 9/2000 | Hang et al. | 250/216 |

FOREIGN PATENT DOCUMENTS

| | | |
|---|---|---|
| DE | 3821422 A1 | 1/1989 |
| DE | 19842153 A1 | 3/2000 |
| JP | 10096862 | 4/1998 |

* cited by examiner

*Primary Examiner*—Constantine Hannaher
*Assistant Examiner*—Otilia Gabor
(74) *Attorney, Agent, or Firm*—Cesari and McKenna, LLP

(57) ABSTRACT

An imaging system comprises three or more sources for providing excitation radiation of different wavelengths, an objective lens for focusing one or more of the exitation wavelengths onto a sample to produce fluorescent emission, and a mirror, configured as a geometric beamsplitter, disposed in the transmission path of the emission radiation and excitation radiation subsequent to reflection from the sample and collimation by the lens, wherein the mirror is utilized to reflect one of the collimated exitation and emission radiation such that the emission is directed to a detector and the collimated exitation is directed away from the detector.

42 Claims, 4 Drawing Sheets ial result. In
IMAGING SYSTEM FOR AN OPTICAL SCANNER

BACKGROUND OF THE INVENTION

1. Field of the Invention

This invention in general relates to optical scanning systems and, in particular, to scanning systems such as fluorescent microarray readers, DNA micro-array readers, or "bio-chip" readers, in which exitation radiation of various wavelengths are used to produce fluorescence in a scanned sample.

2. Description of the Prior Art

The use of exitation radiation to produce fluorescence in a scanned sample is known. U.S. Pat. No. 5,381,224 issued to Dixon et al. discloses scanning optical imaging systems for macroscopic specimens, the system allowing both confocal and non-confocal imaging to be performed in reflected light. Fluorescent imagers are used to acquire data in experiments that utilize fluorescent labels to identify the state of a sample being tested. In some cases the presence of or lack of fluors in the sample determines the experimental result. In other cases the density of the fluors, a function of the intensity of the radiation emitted from the sample, is the measurement of interest and the experimental result can be inferred by measuring the intensity of the detected radiation.

An example of a process that uses fluorescent labels is the microarray. A microarray is a set of experiments involving DNA (or RNA) bound to a glass substrate. Reference or "target" DNA is spotted onto a glass substrate—typically a one-by three-inch glass microscope slide—where it chemically binds to the surface. Each spot, or sample, of DNA constitutes a separate experiment. "Probe" DNA or RNA which has been labeled with a fluorophor is then introduced to the surface of the slide and is allowed to hybridize with the target DNA. Excess probe DNA that does not bind with target DNA is removed from the surface of the slide in a subsequent washing process.

The experiment allows the binding affinity between the probe and target DNA to be measured to determine the likeness of their molecular structures; complementary molecules have a much greater probability of binding than unrelated molecules. The probe DNA is labeled with fluorescent labels that emit a range of radiation energy centered about and including a wavelength $\lambda$ when excited by an external radiation source of a shorter wavelength $\lambda'$. The brightness of emitted radiation is a function of the fluor density in the illuminated sample. Because the fluor density is a function of the binding affinity or likeness of the probe molecule to the target molecule, the brightness of each sample can be mapped as to the degree of similarity between the probe DNA and the target DNA present. On a typical microarray up to tens of thousands of experiments can be performed simultaneously on the probe DNA, allowing for a detailed characterization of complex molecules.

A scanning fluorescent imager divides the area of interest into a set of discrete image elements referred to as pixels. Each pixel is independently addressed and measured for the presence of fluors. The fluors are excited by an incident excitation beam and a portion of the resulting emitted fluorescence radiation is collected and measured by detection apparatus. Each measurement results in a data point that represents the relative fluor density of the measured pixel. The pixel data is then reconstructed to create a quantified representation of the area scanned.

In a scanning microscope, each pixel is illuminated independently while it is being addressed. The light source is typically a laser device focused down to form a spot of the desired size. Radiation is emitted by the fluors in an outward, hemispherical transmission pattern. A portion of this emitted radiation is collected by beam collection optics and directed to the detection apparatus. Additional radiation collected is radiation from the incident excitation beam which is reflected or scattered by the surface of the sample. The imager optics must discriminate between the two radiation wavelengths by rejecting the excitation radiation and passing the fluorescent radiation. Optical filtering components, such as dichroic and bandpass filters, provide the discrimination in conventional systems.

Laser fluorescence micro-array scanners incorporate the ability to deliver multiple laser excitation wavelengths so that fluorescence data can be obtained from the sample at two or more emission wavelengths by detecting two or more fluorescent dyes. Such a unique excitation and emission wavelength pair is typically referred to as a "Channel". Many DNA micro-array samples utilize a two-wavelength scanning method, where the results of one wavelength scan are used as control values and the results of the other wavelength scan represent the desired experimental result, as in Differential Gene Expression. As the market and application mature, and a larger variety of suitable dyes become available, the demand for alternative excitation wavelengths and emission bands will increase.

Most scanning confocal microscopes employ a dichroic or multichroic beamsplitter for color separation between the excitation radiation wavelength X and the emission radiation wavelength $\lambda'$. U.S. Pat. No. 5,672,880 issued to Kain, for example, discloses a fluorescence imaging system in which fluorescent light emitted by a sample is collected by an objective and passed through a dichroic filter placed along the optical axis between a laser and the objective to direct the fluorescent light onto a photo-detector. Dichroic beamsplitters are fabricated using a vacuum deposition process in which inorganic crystalline materials having varying indices of optical refraction are deposited in layers onto optical substrates to create optical filters with specific band-pass and/or band-reject characteristics.

In practice, an optical scanning system may operate utilizing as many as five unique excitation wavelengths and up to ten unique, but variable, emission bands. These operating parameters impose a specification requirement that the component multichroic optical element be designed so as to reflect all five wavelengths and pass the emission wavelengths. A drawback to this approach is that such a specification may be quite difficult to achieve in practice. Moreover, future improvements and developments in optical scanning systems may necessitate that the systems operate with even more excitation and emission wavelengths, requiring a multichroic beamsplitter having an even more demanding specification requirements.

While the art describes a variety of imaging systems for optical scanning, there remains a need for improvements that offer advantages and capabilities not found in presently available scanners, and it is a primary object of this invention to provide such improvements.

It is another object of the present invention to provide an imaging system which can image a sample utilizing three or more different wavelengths of exitation radiation on a single microarray sample.

It is another object of the present invention to provide such an imaging system which does not require a multichroic optical element for operation.

It is further an object of the present invention to provide an optical scanning system which can be adapted for use with newly-available fluors without incurring the is need to reconfigure the imaging system.

Other objects of the invention will be obvious, in part, and, in part, will become apparent when reading the detailed description to follow.

SUMMARY OF THE INVENTION

The present invention discloses an imaging system comprising three or more sources providing exitation radiation of different wavelengths, an objective lens for focusing one or more of the exitation wavelengths onto a sample to produce fluorescent emission, and a mirror, configured as a geometric beamsplitter, disposed in the transmission path of the emission radiation and exitation radiation subsequent to reflection from the sample and collimation by the lens, the mirror reflecting one of the collimated exitation and emission radiation such that the emission is directed to a detector and the collimated exitation is directed away from the detector. Other features of the invention will be readily apparent when the following detailed description is read in connection with the drawings.

BRIEF DESCRIPTION OF THE DRAWINGS

The structure and operation of the invention, together with other objects and advantages thereof, may best be understood by reading the detailed description to follow in connection with the accompanying drawings, of which.

DETAILED DESCRIPTION OF ILLUSTRATIVE EMBODIMENTS

Figure 1:
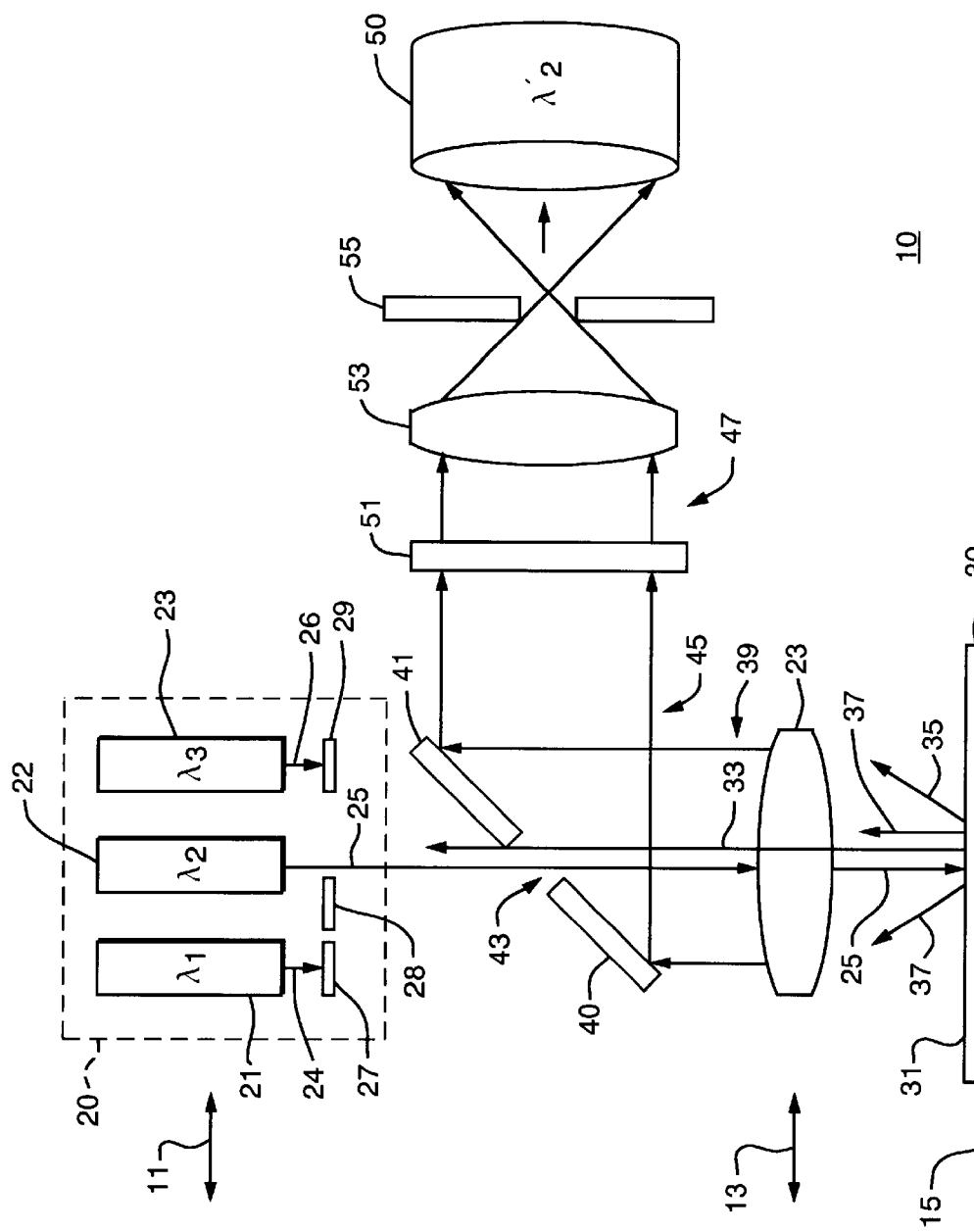
FIG. 1 is a diagrammatic illustration of an imaging system, in accordance with the present invention, the imaging system comprising three exitation radiation sources, an objective lens, and a mirror comprising a centrally-located opening, the mirror utilized for reflecting radiation emitted from a sample to a detector.

There is shown in FIG. 1 an imaging system 10, in accordance with the present invention, as can be utilized in the analysis of a sample 30. Imaging system 10 comprises an illumination array 20 comprising three radiation sources 21, 22, and 23, which can be laser devices or similar monochromatic optical sources, emitting, respectively, exitation beams of radiation 24, 25, and 26 having corresponding wavelengths $\lambda_1$, $\lambda_2$, and $\lambda_3$, for illuminating sample 30. It should be noted that the present invention is not limited to only three radiation sources and additional sources can be used as desired. The illumination provided to sample 30 can be selected by powering only the radiation source(s) desired or, alternatively, radiation sources 21, 22, and 23 can be left in a powered state and one or more shutters 27, 28, and 29 can be moved into or out of the transmission paths of exitation beams 24, 25, and 26 to admit radiation of the desired wavelength and to block other wavelengths. In the example provided, shutter 28 has been moved out of the transmission path of exitation beam 25 so as to allow the projection of radiation having wavelength $\lambda_2$ onto sample 30.

An objective lens 23 is optically designed and positioned between illumination array 20 and sample 30 so as to focus exitation beam 25 to a desired spot size on a surface 31 of sample 30. In a preferred embodiment, the effective focal length of objective lens 23 is approximately 6 millimeters. This provides a spot size of about 5 $\mu$m from an exitation beam 0.6 millimeter in diameter. When projected onto surface 31, excitation beam 25 produces three types of radiation at sample 30. The first type, specular reflection beam 33 having wavelength of $\lambda_2$, is the reflection of a portion of incident exitation beam 25, from surface 31, back along the incident path of transmission. The second type, diffuse reflection 35, also of wavelength $\lambda_2$, is the remaining reflected portion of exitation beam 25. Because it is more scattered, the reflection path of diffuse reflection 35 is not confined to the diameter of the incident path of transmission of exitation beam 25.

The third type, emitted radiation 37, is produced by the illumination of fluors in sample 30 by exitation beam 25. As is well known in the relevant art, such fluors emit radiation when excited by light of a the proper wavelength. Thus, when illuminated by radiation of wavelength $\lambda_1$ (from radiation source 21) or $\lambda_3$ (from radiation source 23), the fluors in sample 30 will emit radiation of wavelength $\lambda'_1$ or $\lambda'_3$ respectively. The wavelength of emitted radiation 37, denoted by $\lambda'_2$, is typically 20 to 40 nm longer than the wavelength $\lambda_2$ of excitation beam 25. By way of example, the energy of excitation beam 25 at surface 31 is on the order of 1 mW, and the energy of emitted radiation 37 is on the order of $10^{-11}$ watts. As can be appreciated by one skilled in the relative art, the signal-to-noise ratio of the emitted to exitation power decreases as the size of specular reflection beam 33 increases and as the amount of diffuse reflection 35 reflected by surface 31 increases.

Specular reflection beam 33 and those portions of diffuse reflection 35 and emitted radiation 37 incident on objective lens 23 are collimated into a composite emission beam 39 comprising radiation of wavelengths $\lambda_2$ and $\lambda'_2$. Preferably, the numerical aperture (NA) of objective lens 23 is made as large as practical so as to intercept the greatest portion of emitted radiation 37, thus to improve the accuracy of the detection process, as explained in greater detail below. In a preferred embodiment, objective lens 23 comprises a numerical aperture of about 0.75.

Composite emission beam 39 is transmitted to a mirror 40. Mirror 40 comprises a reflection surface 41 substantially reflective to radiation of wavelengths $\lambda'_1$, $\lambda'_2$, and $\lambda'_3$. A portion of composite emission beam 39 is reflected from mirror 40 and transmitted to a detector 50 as an attenuated composite emission beam 45. Detector 50 is preferably a photomultiplier tube although an avalanche photodiode or a solid state optical detection device can be used as an alternative device. A photo-multiplier tube typically has high sensitivity and an adjustable gain. The output of the photo-multiplier tube comprises a current that is proportional to the detected radiation power. This current signal is filtered and then converted to a digital value using an analog-to-digital converter.

Where desired, a filter 51, substantially transmissive to emitted radiation, such as radiation of wavelength $\lambda'_2$, and substantially non-transmissive to exitation radiation, such as radiation of wavelength $\lambda'_2$, may be disposed in the transmission path of attenuated composite beam 45. Filter 51 may comprise either a bandpass filter or a long-pass filter. Filter 51 serves to attenuate most or all of diffuse reflection 35 such that an emission beam 47, comprising primarily emitted radiation of wavelength $\lambda'_2$, is transmitted to detector 50. In an alternative embodiment, a focusing lens 53 and an aperture stop 55 may be positioned in the transmission path of emission beam 47 as shown so as to form a confocal system and image emission beam 47 onto detector 50.

Mirror 40 comprises a centrally-located opening 43 positioned in the transmission paths of exitation beam 25 and specular reflection beam 33. Preferably, the width of opening 43 is smaller than the width of emission beam 39 and the size of opening 43 is at least as large the size of specular reflection beam 33. Opening 43 provides for most or all of specular reflection beam 33 to pass back to illumination array 20 rather than being transmitted toward detector 50.

In the present invention, incident excitation beam 25 is scanned across sample 30 by any of three methods. In the first method, illumination array 20 is moved within imaging system 10, as indicated by arrow 11. In the second method, objective lens 23 is translated with respect to sample 30, as indicated by arrow 13. In the third method, sample 30 is laterally translated with respect to imaging system 10, as indicated by arrow 15.

Figure 2:
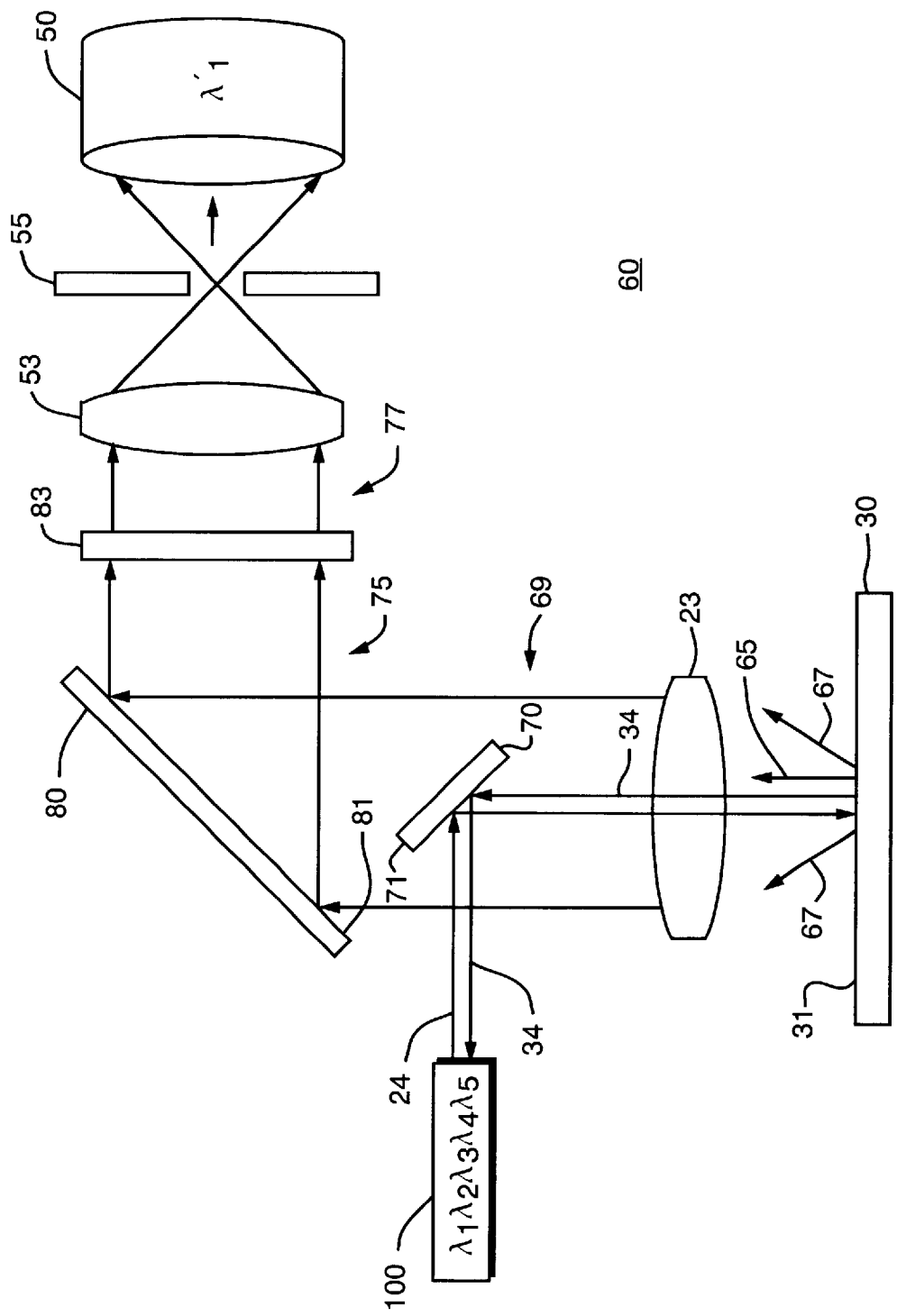
FIG. 2 is a diagrammatic illustration of a preferred embodiment of an imaging system in accordance with the present invention, the imaging system comprising three exitation radiation sources, an objective lens, and a mirror utilized for reflecting exitation radiation to and from the sample and away from the detector.

In the preferred embodiment of the present invention, shown in FIG. 2, an imaging system 60 comprises a mirror 70 disposed between objective lens 23 and an illumination array 100 comprising five radiation sources. Mirror 70 comprises a reflection surface 71 substantially reflective to radiation of wavelengths $\lambda_1$, $\lambda_2$, $\lambda_3$, $\lambda_4$, and $\lambda_5$. In the example shown, exitation beam 24 having wavelength $\lambda_1$ is emitted from illumination array 20, is reflected from mirror 70, and is incident on sample 30 after passing through objective lens 23. A specular reflection beam 33, of wavelength $\lambda_1$ is the reflection of one portion of incident exitation beam 24, from surface 31, and back along the incident path of transmission. Diffuse reflection 65, also of wavelength $\lambda_1$, is the more scattered reflection of the remaining portion of incident exitation beam 24. An emitted radiation 67, of wavelength $\lambda'_1$ is emitted when the fluors in sample 30 are illuminated by incident exitation beam 24. Diffuse reflection 65 and emitted radiation 67 form a composite emission beam 69 transmitted to detector 50.

In an alternative embodiment, imaging system 60 may comprise a secondary mirror 80 emplaced so as to fold the transmission path of composite emission beam 69 and to transmit a reflected composite emission beam 75 to detector 50. By utilizing secondary mirror 80, the cross-sectional profile of imaging system 60 can be reduced for certain applications. Secondary mirror 80 comprises a surface 81 substantially reflective to radiation of wavelengths $\lambda'_1$, $\lambda'_2$, $\lambda'_3$, $\lambda'_4$, and $\lambda'_5$.

In yet another alternative embodiment, there may be disposed a filter 83, substantially transmissive to radiation of wavelength $\lambda'_1$ and substantially non-transmissive to radiation of wavelength $\lambda_1$ in the transmission path of composite emission beam 69 (or in the transmission path of reflected composite emission beam 75, when present). Filter 83 serves to attenuate most or all of diffuse reflection 65 such that an emission beam 77, comprising primarily radiation of wavelength $\lambda'_1$, is transmitted to detector 50. As can be appreciated by one skilled in the relevant art, there may be provided additional filters for each exitation and emission wavelength pair utilized in imaging system 60. In the preferred embodiment, four additional filters (not shown) are utilized in addition to filter 83. Additionally, if desired, imaging system 60 may comprise focusing lens 53 and aperture stop 55 to form a confocal system.

Figure 3:
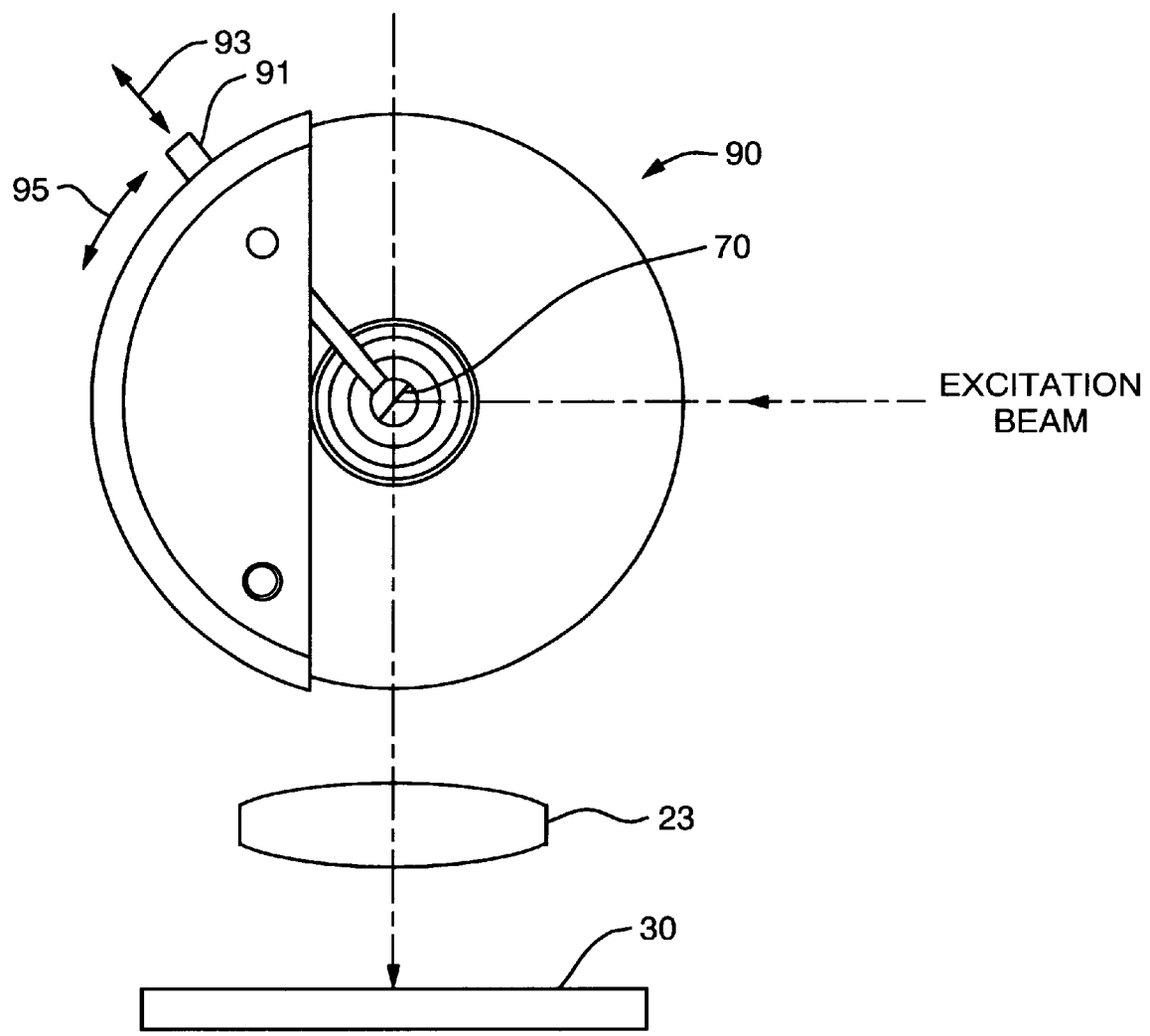
FIG. 3 is a diagrammatical plan view of a supporting structure for the mirror of FIG. 2, the supporting structure comprising features for alignment of the mirror; and, FIG. 4 is a cross-sectional diagram of the lens of FIG. 2, showing the relationship between emission beam width, exitation beam width, and the size of the mirror.

The disclosed embodiments, which advantageously utilize geometric beamsplitting, demonstrate advantages over conventional dichroic and multichroic beamsplitting methods and apparatuses. Where dichroics comprise a glass element designed to reflect particular wavelengths and to transmit others, a geometric beamsplitter comprises a broadband mirror, designed to reflect excitation or emission radiation, and physically sized to provide for detection of the maximum amount of emission radiation. The broadband mirror, which comprises a major dimension larger than the width of the excitation beam, is placed about 45° with respect to the transmission path of the exitation beam. By providing an angularly-adjustable spherical mount 90, as shown in FIG. 3, all necessary degrees of adjustability for the optical alignment of the excitation beam are available. When properly aligned, mirror 70 will completely capture the specular reflection of the excitation beam and redirect the specular component of the radiant energy away from the detector and, preferably to the radiation sources, thus enhancing the system signal-to-noise ratio. Alignment is achieved by means of a post 91 which is configured so as to have six degrees of freedom. For example, positioning of mirror 70 is accomplished by a radial movement of post 91, as indicated by arrow 93, and the pitch, roll, and yaw of mirror 70 is adjusted by suitable rotation of post 91, where one such adjustment is indicated by arrow 95.

Figure 4:
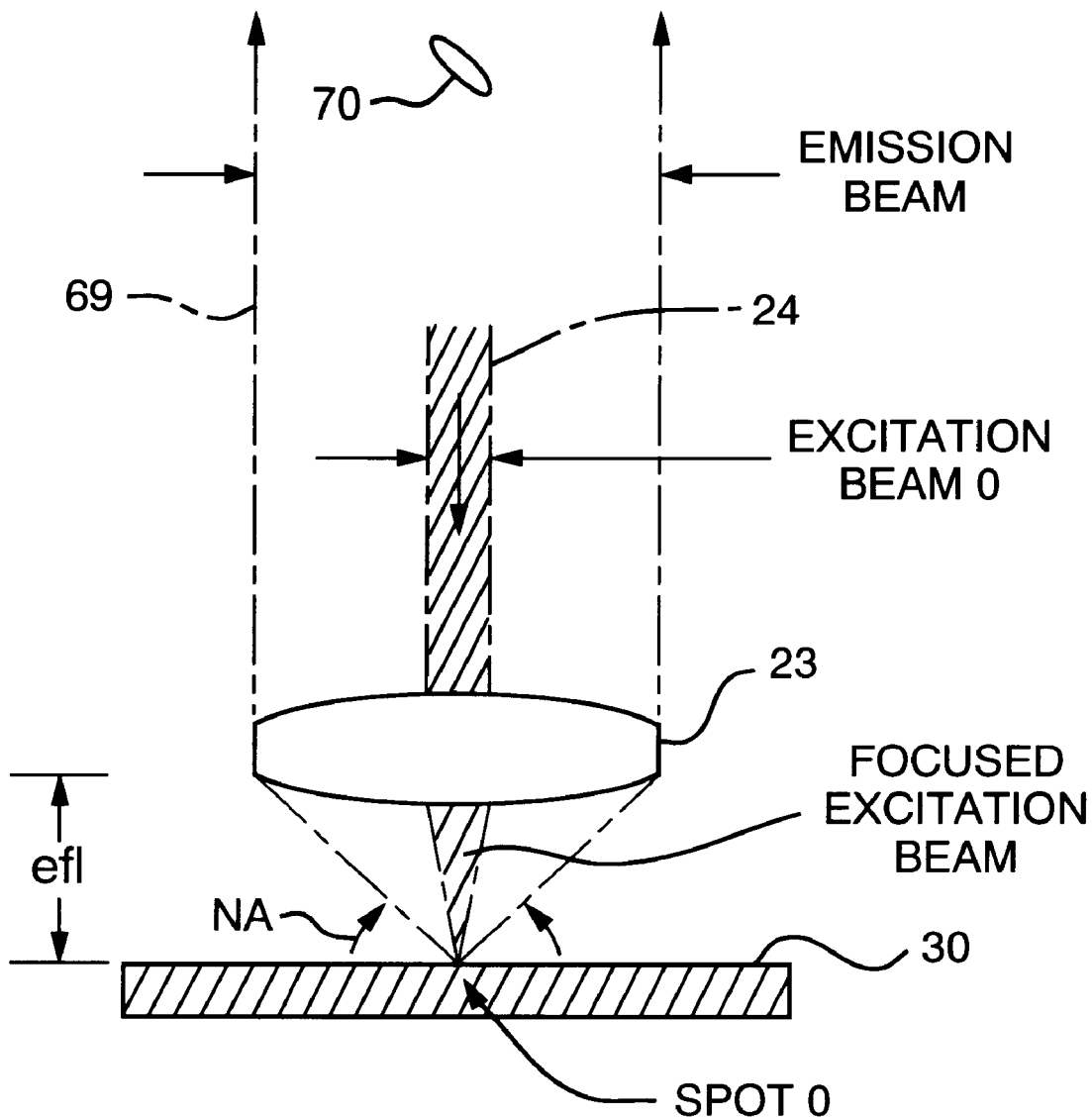

The relationship of the numerical aperture of objective lens 23 to a geometric emission transmission factor (GETF) can be best explained with reference to FIGS. 2 and 4. GETF is defined as the ratio of: i) the blockage of composite emission beam 69 resulting from placement of mirror 70 (and associated mounting components) in the transmission path of emission beam 69, and ii) the overall path diameter of emission beam 69. It can be shown, with the following two examples, that a higher numerical aperture will improve the GETF of a particular imaging system.

The spot size of incident exitation beam 24, having a beam diameter of 0.6 millimeter (using a HeNe laser device as an example) is specified to be approximately 5 μm. This requires that objective lens 23 have an effective focal length of about 6 millimeters. For an NA of 0.75, the aperture diameter is about 13.6 millimeters and the aperture area is about 145.26 mm². If the broadband mirror and its mount have a diameter of 3.17 mm, and are set at a 45° angle with respect to the emission path, the area of blockage is about 5.57 mm². The GETF is determined to be:

$$GETF = \frac{145.26 \text{ mm}^2}{5.57 \text{ mm}^2} = 26.07$$

For an objective lens having an effective focal length of 10 millimeters and an NA of 0.30, the aperture diameter is about 6.2 millimeter for an aperture area of 30.19 mm. To produce a 5 μm excitation spot, the input exitation beam should be about 1.0 millimeter. A broadband mirror having a diameter of 2.0 millimeter will captures the input exitation beam completely and allow for some tolerance in position. If the broadband mirror is set at a 45° angle with respect to the emission path, the area of blockage is about 2.22 mm². In this case the GETF is determined to be:

$$GETF = \frac{30.19 \text{ mm}^2}{2.22 \text{ mm}^2} = 13.06$$

That is, the GETF is reduced by a factor of two, demonstrating that the GETF is a function of both lens NA and effective focal length. The exitation spot size is related to the effective focal length and the emission aperture is related to the NA.

While the invention has been described with reference to particular embodiments, it will be understood that the present invention is by no means limited to the particular constructions and methods herein disclosed and/or shown in the drawings, but also comprises any modifications or equivalents within the scope of the claims.

What is claimed is:

1. An imaging system, suitable for use in optically scanning a sample, said imaging system comprising:
a plurality of n radiation sources, where $n \geq 3$, at least one said radiation source providing a corresponding excitation beam comprising radiation of wavelength $\lambda_i$, where $1 \leq i \leq n$;
an objective lens disposed between said radiation sources and the sample such that said $\lambda_i$ excitation beam passes through said objective lens and illuminates the sample, whereby at least a portion of said $\lambda_i$ excitation beam incident upon the sample is converted into and subsequently emitted as radiation of wavelength $\lambda_i'$, said objective lens further disposed to substantially collimate at least a portion of said $\lambda_i'$ emitted radiation so as to form a corresponding emission beam of radiation of wavelength $\lambda_i'$ transmitted away from the sample;
a detector responsive to radiation of wavelength $\lambda_i'$; and,
a geometric beam splitter disposed in the transmission path of said emission beam between said plurality of radiation sources and said objective lens and oriented to provide at least a portion of said excitation beam in the direction of said objective lens and at least a portion of said emission beam to said detector based on the differences in the relative positions of said emission beam and said excitation beam at said geometric beam splitter.

2. The imaging system of claim 1 wherein said radiation sources comprise laser devices.

3. The imaging system of claim 1 wherein said objective lens comprises a numerical aperture of at least 0.5.

4. The imaging system of claim 1 wherein said detector produces an electrical signal in response to incident radiation of wavelength $\lambda_i'$.

5. The imaging system of claim 1 wherein said geometric beamsplitter comprises a major dimension at least as large as the width of said emission beam.

6. The imaging system of claim 1 wherein said geometric beam splitter includes a centrally-located opening, said opening disposed within the transmission path of said emission beam such that at least a portion of said excitation beam reflected from the sample passes through said objective lens and said opening and away from said detector.

7. The imaging system of claim 6 wherein the width of said opening is smaller than the width of said emission beam.

8. The imaging system of claim 1 further comprising means for scanning at least one of said exitation beams across the sample.

9. The imaging system of claim 8 wherein said means for scanning comprises means for moving said radiation sources within said imaging system.

10. The imaging system of claim 8 wherein said means for scanning comprises means for translating said objective lens relative to the sample.

11. The imaging system of claim 8 wherein said means for scanning comprises means for translating the sample relative to said imaging system.

12. The imaging system of claim 1 further comprising means for selectively blocking said exitation beams such that only one exitation beam illuminates the sample.

13. The imaging system of claim 12 wherein said means for selectively blocking comprises a shutter.

14. The imaging system of claim 1 further comprising a filter disposed in the transmission path of said emission beam, said filter substantially transmissive to radiation of wavelength $\lambda_i'$ and substantially non-transmissive to radiation of wavelength $\lambda_i$.

15. The imaging system of claim 1 wherein said detector comprises at least one member of the group consisting of a photomultiplier tube, an avalanche photodiode, and a solid state optical detector.

16. An imaging system, suitable for use in optically scanning a sample, said imaging system comprising:
a plurality of n radiation sources, where $n \geq 3$, at least one said radiation source providing a corresponding excitation beam comprising radiation of wavelength $\lambda_i$, where $1 \leq i \leq n$;
an objective lens disposed between said radiation sources and the sample such that said $\lambda_i$ excitation beam passes through said objective lens and illuminates the sample, whereby at least a portion of said $\lambda_i$ excitation beam incident upon the sample is converted into and subsequently emitted as radiation of wavelength $\lambda_i'$, said objective lens further disposed to substantially collimate at least a portion of said $\lambda_i'$ emitted radiation so as to form a corresponding emission beam of radiation of wavelength $\lambda_i'$ transmitted away from the sample;
a detector responsive to radiation of wavelength $\lambda_i'$; and,
a geometric beam splitter disposed in the transmission path of said excitation beam between said radiation sources and said objective lens so as to direct said excitation beam onto the sample, said geometric beam splitter being sized and oriented so as to direct to said radiation source at least a portion of said excitation beam of wavelength $\lambda_i$ reflected from said sample and subsequently transmitted through said objective lens, said geometric beam splitter directing said excitation beam and said reflected excitation beam based on the relative position of the beams with respect to said emission beams, said geometric beam splitter further allowing at least a portion of said emission beam to pass to said detector.

17. The imaging system of claim 16 wherein said radiation sources comprise laser devices.

18. The imaging system of claim 16 wherein said objective lens comprises an numerical aperture of at least 0.5.

19. The imaging system of claim 16 wherein said detector produces an electrical signal in response to incident radiation of wavelength $\lambda_i'$.

20. The imaging system of claim 16 wherein said geometric beam splitter comprises a width approximately equal to the width of said excitation beam.

21. The imaging system of claim 16 further comprising means for scanning at least one of said exitation beams across the sample.

22. The imaging system of claim 21 wherein said means for scanning comprises means for moving said radiation sources within said imaging system.

23. The imaging system of claim 21 wherein said means for scanning comprises means for translating said objective lens relative to the sample.

24. The imaging system of claim 21 wherein said means for scanning comprises means for translating the sample relative to said imaging system.

25. The imaging system of claim 16 further comprising means for selectively blocking said exitation beams such that only one exitation beam illuminates the sample.

26. The imaging system of claim 25 wherein said means for selectively blocking comprises a shutter.

27. The imaging system of claim 16 farther comprising a filter disposed in the transmission path of said emission beam, said filter substantially transmissive to radiation of wavelength $\lambda_i'$ and substantially non-transmissive to radiation of wavelength $\lambda_i$.

28. The imaging system of claim 16 wherein said detector comprises at least one member of the group consisting of a photomultiplier tube, an avalanche photodiode, and a solid state optical detector.

29. An imaging system, suitable for use in optically scanning a sample, said imaging system comprising:

five laser devices, said laser device providing excitation beams comprising radiation of wavelength $\lambda_1$, $\lambda_2$, $\lambda_3$, $\lambda_4$, and $\lambda_5$ respectively;

means for selecting any of said excitation beams so as to provide radiation comprising at least a wavelength of $\lambda_1$;

an objective lens disposed between said laser devices and the sample such that said excitation beam comprising radiation of $\lambda_1$ passes through said objective lens and illuminates the sample whereby at least a first portion of said excitation beam comprising radiation of $\lambda_1$ and incident upon the sample is converted into and emitted as radiation of wavelength $\lambda_1'$ and a second portion of said excitation beam is reflected from the sample as a specular reflection beam, said objective lens further disposed to substantially collimate at least a portion of said emitted radiation and said specular reflection beam so as to form a corresponding emission beam of radiation comprising wavelengths $\lambda_1'$ and $\lambda_1$ transmitted away from the sample;

a photomultiplier tube responsive to radiation of wavelength $\lambda_1'$; and, a geometric beam splitter disposed in the transmission path of said emission beam between said laser devices and said objective lens and oriented to reflect at least a portion of said specular reflection beam to said laser devices and to pass at least a portion of said emission beam to said detector based on the relative positions and sizes of said specular reflection beam and said emission beam at said geometric beam splitter.

30. The imaging system of claim 29 wherein said objective lens comprises a focal length of approximately 6 millimeters.

31. The imaging system of claim 29 wherein said objective lens comprises a numerical aperture of approximately 0.75.

32. The imaging system of claim 29 wherein said detector comprises at least one member of the group consisting of a photomultiplier tube, an avalanche photodiode, and a solid state optical detector.

33. The imaging system of claim 29 further comprising a filter disposed in the transmission path of said emission beam, said filter substantially transmissive to radiation of wavelength $\lambda_1'$ and substantially non-transmissive to radiation of wavelength $\lambda_1$.

34. The imaging system of claim 29 further comprising means for scanning at least one of said exitation beams across the sample.

35. A method for optically scanning a sample, said method comprising the steps of:

providing n radiation beams, each said beam comprising a respective wavelength of $\lambda_i$, where $n \geq 3$ and $1 \leq i \leq n$;

focusing a selected one of said radiation beams comprising a wavelength of $\lambda_i$ onto the sample by means of an objective lens such that at least a portion of said selected radiation beam is converted into radiation comprising a wavelength of $\lambda_i'$, said converted radiation emitted from the sample as emitted radiation of wavelength $\lambda_i'$;

collecting at least a portion of said emitted radiation of wavelength $\lambda_i'$ and at least a portion of beam radiation of wavelength $\lambda_i$ reflected from the sample;

collimating said collected radiation and transmitting said collimated radiation to a geometric beam splitter along a path of transmission, said geometric beam splitter comprising a surface disposed at an angle to the transmission path of said collimated radiation; and, transmitting at least a portion of said emitted radiation included in said collimated radiation to a detector by directing said portion of said emitted radiation by reflection or around said geometric beam splitter based on the position or width of said portion of said emitted radiation relative to the position or width of said radiation beams at said geometric beam splitter.

36. The method of claim 35 wherein said geometric beam splitter comprises a major dimension smaller than the width of said collimated beam such that a portion of said beam radiation of wavelength $\lambda_i$ reflected from the sample and collimated by said objective lens is deflected by said geometric beam splitter away from said path of transmission.

37. The method of claim 36 further comprising the step of reflecting said selected radiation beam to said objective lens by means of said geometric beam splitter prior to said step of focusing said selected radiation beam.

38. The method of claim 35 wherein said geometric beam splitter includes an opening such that portion of said beam radiation of wavelength $\lambda_i$ reflected from the sample and collimated by said objective lens passes through said opening and is transmitted away from said detector.

39. The method of claim 38 wherein said step of transmitting at least a portion of said emitted radiation to a detector is accomplished by means of said beam splitter.

40. An imaging system, suitable for use in optically scanning a sample, said imaging system including:

A) a plurality of n radiation sources that each provide a relatively narrow diameter excitation beam of wavelength $\lambda_i$, where $1 \leq i \leq n$;

B) an objective lens disposed between the radiation sources and the sample such that said $\lambda_i$ excitation beam passes through the objective lens and illuminates the sample, whereby at least a portion of the $\lambda_i$ excitation beam incident upon the sample is converted into and subsequently emitted as radiation of wavelength $\lambda_i^\circ$ and a portion of the excitation beam is reflected by the sample, the objective lens further disposed to substantially collimate at least a portion of the $\lambda_i'$ emitted radiation and the reflected light; and C) a geometric beam splitter disposed in the transmission path of the excitation beam between the radiation sources and the objective lens, the beam splitter including a feature that has a diameter that corresponds to the relatively narrow diameter of the excitation beam, the feature i) re-directing at least a large portion of the excitation beam and the associated collimated reflected light, or ii) allowing at least a large portion of the excitation beam and the associated collimated reflected light to pass through the beam splitter.

41. The imaging system of claim 40 wherein the feature is the diameter of the beamsplitter, and the beam splitter further includes a mirrored surface for re-directing, the collimated emitted radiation passing outside the diameter of the beamsplitter.

42. The imaging system of claim 40 wherein the feature is a hole that is positioned to pass at least a large portion of the excitation beam and the collimated reflected light, and the beam splitter further includes a mirrored surface for re-directing at least a large portion of collimated emitted radiation.

* * * * *